United States Patent [19]

Dalla Betta et al.

[11] 4,002,658
[45] Jan. 11, 1977

[54] METHANATION CATALYST AND PROCESS OF USING THE SAME

[75] Inventors: Ralph A. Dalla Betta, Dearborn; Ann G. Piken, West Bloomfield; Mordecai Shelef, Southfield, all of Mich.

[73] Assignee: Ford Motor Company, Dearborn, Mich.

[22] Filed: May 1, 1975

[21] Appl. No.: 573,716

[52] U.S. Cl. .......................... 260/449 M; 252/472
[51] Int. Cl.² ...................... C07C 1/04; B01J 23/74
[58] Field of Search ................ 252/472; 260/449 M

[56] References Cited

UNITED STATES PATENTS

| | | | |
|---|---|---|---|
| 943,627 | 12/1909 | Elworthy | 260/449 M |
| 1,643,663 | 9/1927 | Klatte et al. | 260/449 M |
| 2,251,000 | 7/1941 | Pyzel | 260/449.6 M |
| 3,498,927 | 3/1970 | Stiles | 252/472 |
| 3,531,543 | 9/1970 | Clippinger et al. | 252/472 |
| 3,847,963 | 11/1974 | LaLancette | 260/449 M |

OTHER PUBLICATIONS

Chemical Abstracts, vol. 81, 1974, p. 378, 69061k.
Chemical Abstracts, vol. 69, 1968, p. 2858, 30518s.

*Primary Examiner*—Patrick P. Garvin
*Assistant Examiner*—William G. Wright
*Attorney, Agent, or Firm*—William E. Johnson; Keith L. Zerschling

[57] ABSTRACT

This application teaches a methanation catalyst in which nickel is employed on a zirconium oxide substrate. This catalyst may be used in a methanation process in which the feed gases to the process contain between about 10 to 100 ppm (parts per million) of sulfur.

2 Claims, No Drawings

METHANATION CATALYST AND PROCESS OF USING THE SAME

BACKGROUND OF THE INVENTION

Substitute natural gas may be prepared by a coal gasification process. A general discussion of coal gasification is set forth in *Environmental Science and Technology*, December 1971, Vol. 5, No. 12 in an article entitled "Gas from Coal, Fuel of the Future" by G. Alex Mills. Generally in the methanation portion of a coal gasification process, nickel is used as a catalyst to convert the synthesis gas, CO and $H_2$, produced in the gasification step into methane as the final product.

The prior art teaches the placement of the nickel catalyst on an aluminum oxide substrate. When nickel is used on an aluminum oxide substrate, it is necessary to remove substantially all of the sulfur contained in the feed gas to the methanator. In particular, it is necessary to reduce the sulfur content of the feed gas to a level of less than about 0.1 ppm because the sulfur poisons the catalyst if present in any higher concentration. In order to achieve such a low sulfur content in the feed gas, it is necessary to clean initially the feed gas in a hot carbonate scrubbing operation or any other of a number of cleaning operations which reduces the sulfur to a level in the range of from 10 to 100 ppm. A second cleaning is necessary to reduce the sulfur concentration of the gas below 0.1 ppm. This second step is generally accomplished by an absorption process, whereby the sulfur is absorbed in zinc oxide, iron oxide or a number of other materials.

Sulfur is found in the feed gas to the methanator because sulfur is found in most coal supplies. On the average, the synthesis gas produced in a coal gasification process will contain at least 3,000 ppm sulfur prior to any sulfur removal treatment. The treatment of this gas to remove sulfur is a costly operation and when the treatment entails a two step removal process, the cost is increased. The process step of removing the sulfur from 10 to 100 ppm down to less than 0.1 ppm is very costly because of the large volume of gas which is processed to remove small amounts of sulfur and the expense of replacement or recovery of the absorbent.

It is an object of this invention to provide a methanation catalyst which is not easily poisoned by sulfur. It is a further object of this invention to provide a methanation process in which the gas fed to the process can contain in the range from 10 to 100 ppm of sulfur and can contain substantially higher sulfur levels for short periods of time.

SUMMARY OF THE INVENTION

This invention relates to a catalyst for a methanation operation, and, also to a process of methanating a suitable feed gas stream.

In accordance with one aspect of the teaching of this invention, a catalyst for a methanation operation includes a substrate formed of zirconium oxide and a catalyst material thereon of nickel. The nickel is present on the zirconium oxide in a range from 0.5% to 60% by weight, and, preferably, in a range from 20 to 50 percent by weight.

In accordance with another aspect of this invention, a synthesis gas stream prepared by gasifying coal is processed to remove sulfur therefrom by a single sulfur removal operation. The resulting synthesis gas stream contains in a range from 10 to 100 ppm of sulfur. This synthesis gas is passed over a methanation catalyst in which the substrate is zirconium oxide and the catalyst material is nickel. Even at the relatively high sulfur concentrations of 10 to 100 ppm, the methanation process is effective to produce substantial quantities of methane gas from the feed gas.

DESCRIPTION OF THE PREFERRED EMBODIMENT

Catalyst Preparation

A specific method for preparing a catalyst in accordance with the teachings of this invention is as follows. A high surface area zirconia ($ZrO_2$) powder, having a surface of about 80 square meters per gram is contacted with an aqueous solution of nickel nitrate $Ni(NO_3)_2$. Only enough nickel nitrate solution is used to just wet the zirconia. The zirconia powder, with the solution thereon, is dried in air at about 100° C to remove the moisture therefrom. The material is reduced in hydrogen gas at about 450° C in order to reduce the nickel to nickel metal on the zirconia base. The catalyst is stabilized by cooling it slowly in hydrogen gas to room temperature, removing the hydrogen gas by introduction of nitrogen gas and then by slowly adding oxygen. The slow addition of oxygen results in oxidation of the nickel on the surface without unnecessarily overheating the catalyst. After this preparation, the catalyst may be handled and it is ready for use in a methanation operation. However, prior to the actual methanation operation, it is necessary to re-reduce the surface nickel oxide by heating the same in hydrogen gas from 300° to 450° C.

The amount of nickel placed on the zirconia substrate can be varied from very low concentrations of metal, from about 0.5% by weight, to very high concentrations of up to 60% nickel by weight. The preferred range of nickel concentration is in the range from 20 to 50 percent by weight. If desired, as an optional step, the catalyst material may be calcined after the nickel nitride solution has been dried thereon. This step is carried out before the reduction step. The important part of preparing the catalyst is that zirconium oxide is used as the substrate.

The substrate zirconium oxide and resulting catalyst may exist in any number of forms. The original zirconium oxide may be in the form of pellets of any size and shape which are then impregnated with a solution containing nickel and then dried and/or calcined and reduced. A second form may be to coat a monolithic honeycomb support structure with a zirconium oxide slurry to form a zirconium oxide layer on the support surface. The support structure may consist of a metal, metal oxide such as cordierite, alumina, silica, silicon nitride, silicon carbide or any other number of materials. After coating the support structure with the zirconium oxide layer, it is dried and/or calcined. Nickel is then added to the coated structure by impregnation with a nickel containing solution.

The catalyst product of this invention can be used in a methanation operation carried out on gaseous products produced as the result of coal gasification. The catalyst is effective even though the feed gas to the methanator contains 10 to 100 ppm of sulfur. Such a level of sulfur generally remains from coal gasification feed stock after that feed stock has been subjected to a hot carbonate scrubbing operation to remove therefrom the originally substantially higher quantities of sulfur in the range from 3000 ppm to 5000 ppm.

Operating Conditions

Tests were carried out on a 5% nickel zirconia catalyst and a 2% nickel aluminate ($Al_2O_3$) catalyst. The results of the test are shown in Table 1.

Table 1

Effect of $H_2S$ on Rate of CO Methanation
(400° C, $H_2/CO$ = 3.8, $P_{H_2} + P_{CO}$ = 0.75 atm)

| $H_2S$ level | Rate × $10^2$ (Turnover number, $S^{-1}$) | |
|---|---|---|
| | 5% $Ni/ZrO_2$ | 2% $Ni/Al_2O_3$ |
| Steady-state | 2.21 | 7.98 |
| 1 ppm $H_2S$ | 0.349 | 0.313 |
| 5 ppm $H_2S$ | 0.671 | 0.176 |
| 10 ppm $H_2S$ | 0.826 | 0.168 |
| 193 ppm $H_2S$ | 1.00 | |
| 1000 ppm $H_2S$ | 0.561 | |

The important points to be noted from Table 1 are as follows. The rate of CO hydrogenation in $Ni/Al_2O_3$ decrease by a factor of 20 in the presence of 1 ppm $H_2S$ while the activity of the $Ni/ZrO_2$ catalyst first decreases then increases as $H_2S$ level is increased. The activity in the range of 10 to 200 ppm is approximately half that in the absence of $H_2S$. Although the $Ni/Al_2O_3$ catalyst starts at a higher activity, at 10 ppm $H_2S$ the $Ni/ZrO_2$ catalyst is five times more active than the $Ni/Al_2O_3$ catalyst. Exposure of the $Ni/ZrO_2$ catalyst to very high levels of $H_2S$, e.g., 1000 ppm, lowers the activity but as $H_2S$ is decreased the activity increases to its former level. This reversibility implies the catalyst would not be affected by accidental sulfur breakthrough due to failure of pretreatment equipment upstream of the methanator reactor.

In actual operating conditions for a commercial methanator reactor, the temperature of operation could be in the range from 250° to 700° C. The pressure for operation could be in the range from 20 to 100 atmospheres. In general, the feed gas for the methanator reactor could have the following formulation: hydrogen 45% by volume, carbon monoxide 15% by volume, carbon dioxide 20% by volume, methane 20% by volume and water at a vol/vol ratio of 0.5. Hydrogen sulfide or carbonyl sulfide can make up to 100 ppm of the feed gases. These feed gases can be achieved by an ordinary coal gasification process with the treatment of the so produced gases by any number of commercial cleaning apparatus such as a hot carbonate scrubbing operation to remove the heavy sulfur concentrations. Prior known catalyst, namely Ni on $Al_2O_3$, require the sulfur be reduced to a level of less than 0.1 parts per million which requires the treatment of the gas after the hot carbonate scrubbing operation by an additional step namely absorption on a metal oxide.

Other elements may also be added to the nickel zirconia catalyst to improve the same. Such additions are known in the art for the purpose of improving the catalyst life, or for making the catalyst resistant to various trace materials which can poison the catalyst over long periods of exposure.

There has been disclosed herein a nickel zirconia catalyst useful for methanation of a feed gas stream having relatively a high sulfur content. There has also been disclosed herein a process for methanating a feed gas stream containing a relatively high concentration of sulfur. In view of the teachings of the specification, those skilled in the art will make many modifications of this invention which do not depart from the true spirit thereof. It is intended that all such modifications be included within the scope of the appended claims.

We claim:

1. A method of methanating a synthesis gas stream including a sulfur bearing component in a concentration in a range from 10 ppm to 100 ppm which comprises: passing said synthesis gas stream over a nickel catalyst formed on a catalyst substrate principally of zirconium oxide.

2. The method of claim 1 wherein: said synthesis gas stream is obtained by gasification of coal, and wherein said synthesis gas stream is subjected to a single sulfur removal operation prior to the methanation operation.

* * * * *